United States Patent [19]

Gardineer et al.

[11] 4,392,486

[45] Jul. 12, 1983

[54] COMBINATION VANITY SCREEN AND PATIENT SUPPORT COUCH EXTENSION

[75] Inventors: Bayard G. Gardineer, Skillman; James A. Heringes, Dayton, both of N.J.

[73] Assignee: Technicare Corporation, Solon, Ohio

[21] Appl. No.: 296,092

[22] Filed: Aug. 26, 1981

[51] Int. Cl.$^3$ .............................................. A61F 5/00
[52] U.S. Cl. ........................................ 128/68; 108/6; 108/60; 128/70
[58] Field of Search .................................. 128/69–74; 269/323–326; 5/3–5, 53 B–53 D, 512, 163; 108/5, 6, 60, 16, 17, 152; 144/285–287; 312/281, 282, 241, 313, 316; 211/88; 272/79, 80, 144; 273/85 R; 160/135; 297/184

[56] References Cited

U.S. PATENT DOCUMENTS

| | | | |
|---|---|---|---|
| 1,233,607 | 7/1917 | Ryan | 108/28 |
| 4,089,522 | 5/1978 | Rock | 108/6 X |
| 4,237,796 | 12/1980 | Gordon et al. | 312/239 X |

Primary Examiner—Richard J. Apley
Assistant Examiner—David J. Brown

Attorney, Agent, or Firm—Donal B. Tobin

[57] ABSTRACT

A combination vanity screen and patient support couch extension. The vanity screen includes two overlapping panels, an upright support panel and a pivoting extension panel. The overlapping edge of the support panel is hinged to the back of the extension panel so that the extension panel may pivot from an upright position in generally coplanar alignment with the support panel to a horizontal position in generally coplanar alignment with the primary patient support couch so as to act as a support couch extension. The upright panel and the extension panel are locked in a coplanar relationship by a door knob which includes a bolt and a striker plate mounted in confronting relationship on the upright panel and the overlapping edge of the extension panel. The free end of the extension panel includes a support bar, which rests on projections extending from the primary support couch, and a latch, which locks the free end of the extension panel to the projections so that the couch extension may be locked in the horizontal position. A counterbalance mechanism is provided to facilitate the movement of the extension panel between its vertical and horizontal positions.

10 Claims, 11 Drawing Figures

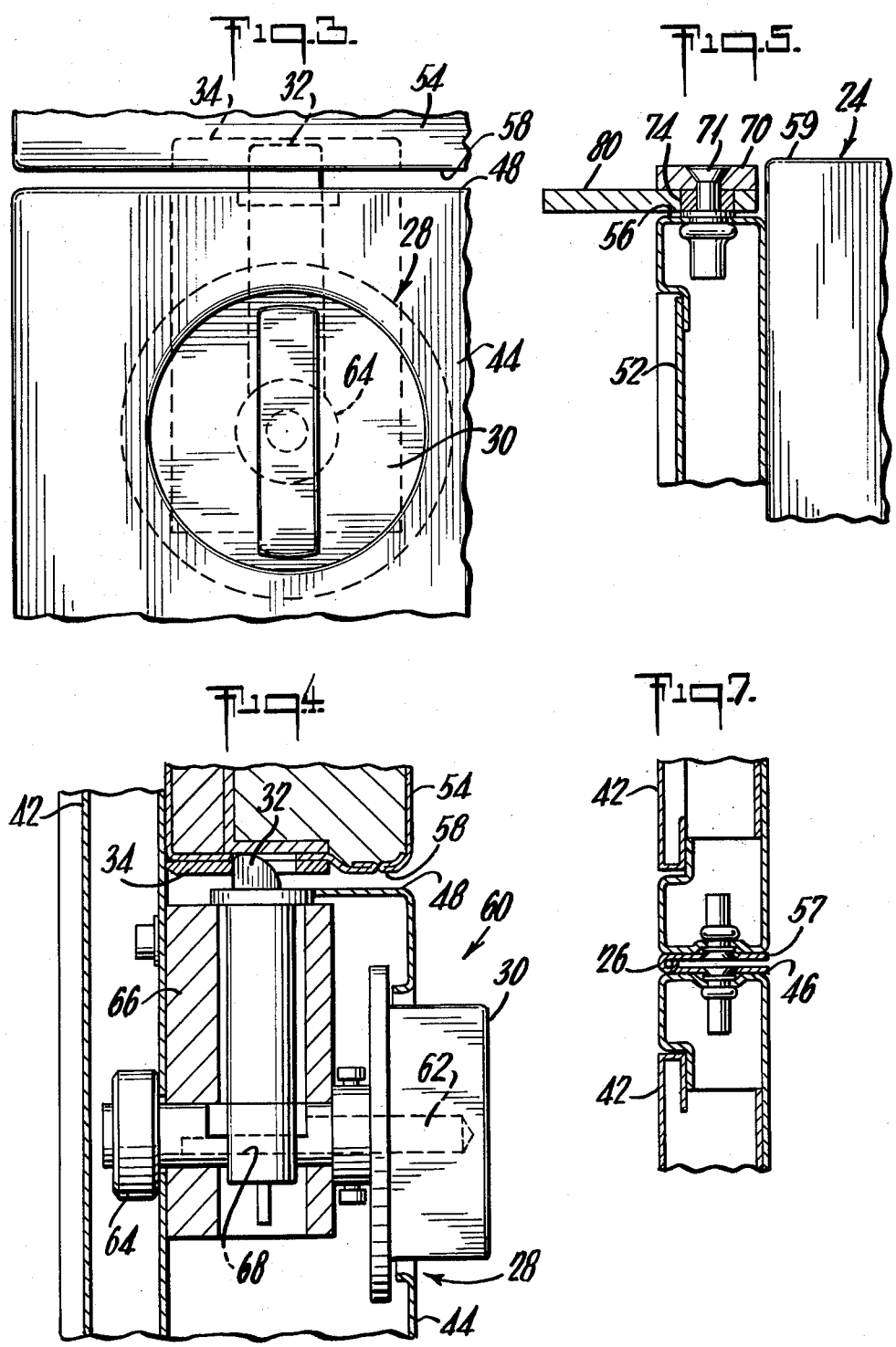

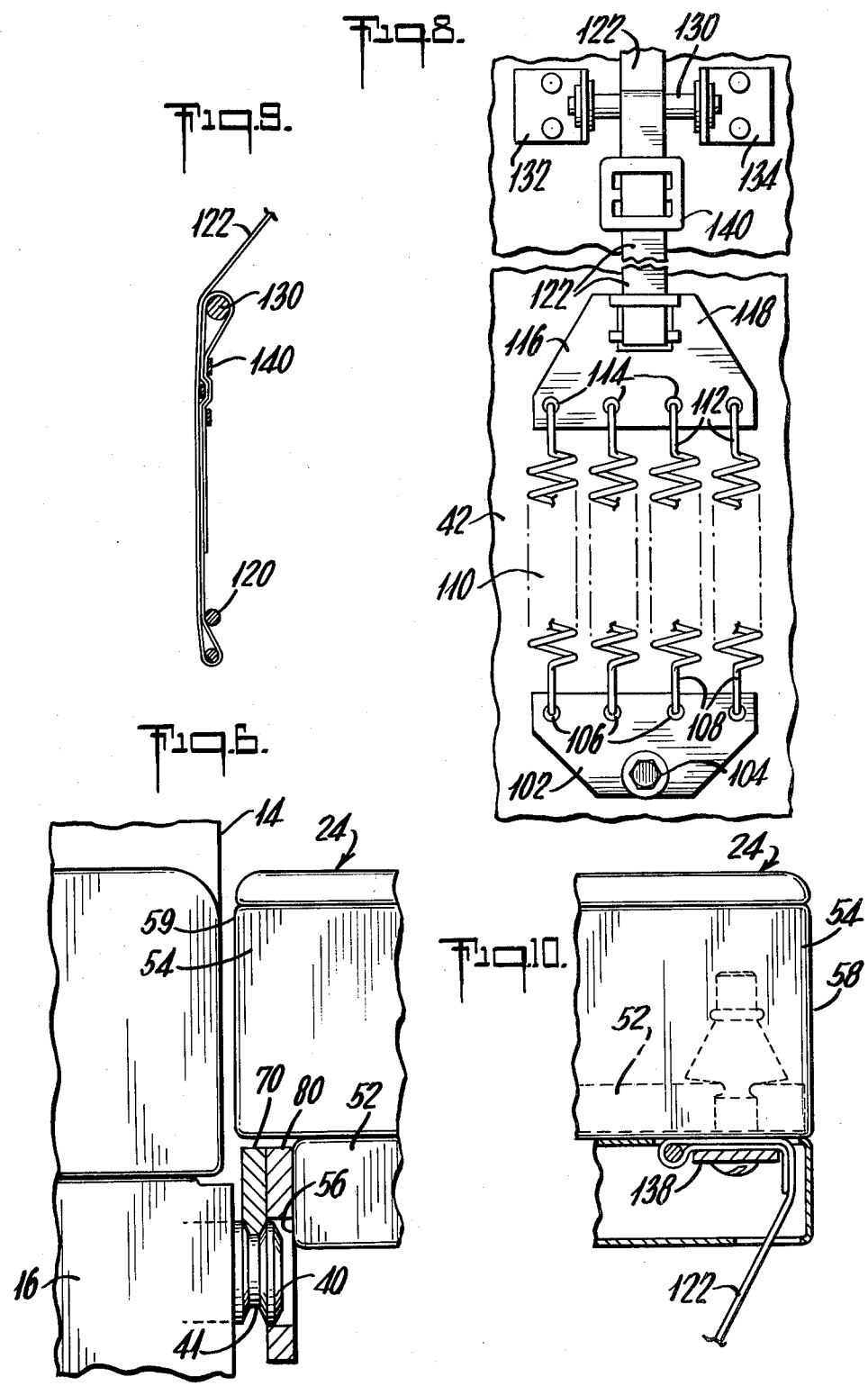

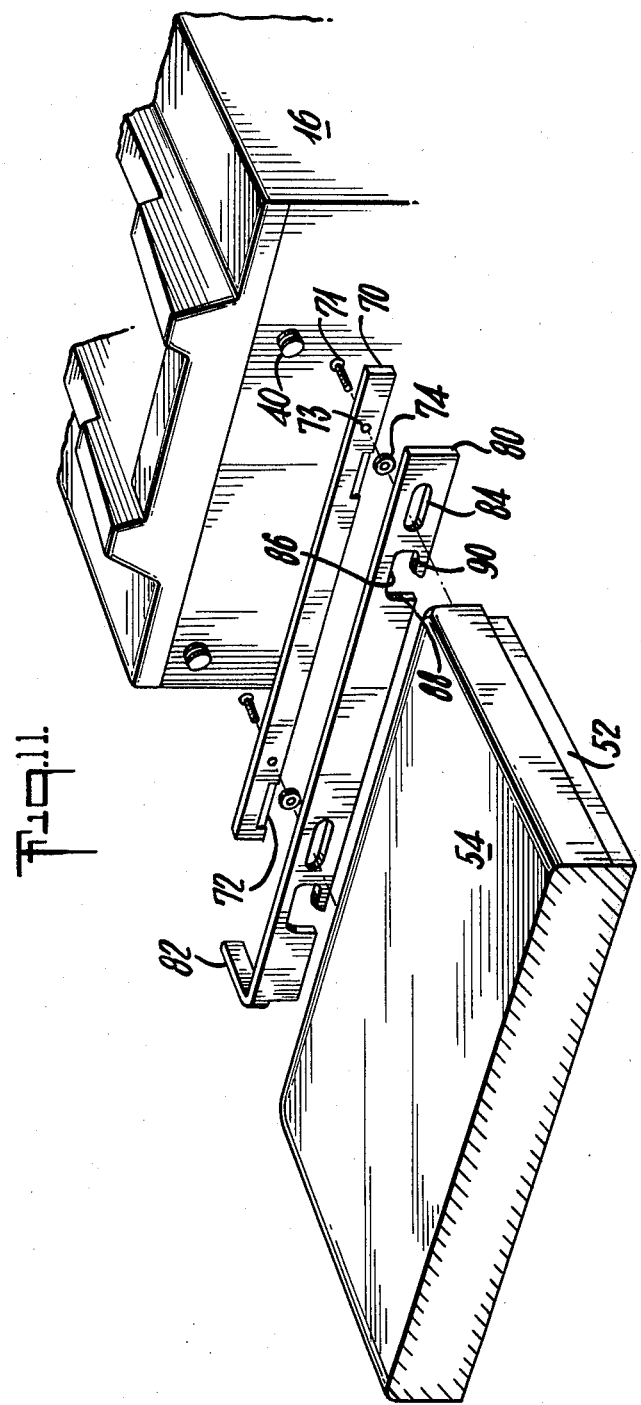

COMBINATION VANITY SCREEN AND PATIENT SUPPORT COUCH EXTENSION

FIELD OF THE INVENTION

This invention relates to a combination vanity screen and patient support couch extension and, more particularly, to an apparatus comprising two overlapping panels which may be locked together in a vertical coplanar relationship to form a vanity screen or locked to a primary patient support apparatus in a perpendicular orientation to provide a horizontal patient support extension.

BACKGROUND OF THE INVENTION

With present day medical diagnostic equipment, it is often necessary to support the patient in a variety of orientations for proper examination or for the comfort of the patient. One such medical diagnostic instrument is disclosed in the applicants' copending Patent Application Ser. No. 129,814, filed Mar. 12, 1980, entitled "Patient Support Apparatus for Ultrasound Mammary Scanning Apparatus." This patent application is assigned to the assignee of the present invention. The specification of that application is incorporated by reference herein.

By way of summary, that application relates to an apparatus for supporting a patient during diagnosis of the patient's breast and surrounding axilla region with an ultrasound imaging system. The support apparatus is particularly adapted to examining the patient's breast while the breast is suspended.

A patient support platform is supported on top of a cabinet enclosing the ultrasound system. This patient support platform is a primary patient support platform which supports the patient's upper body above the waist in the horizontal position so that the breast may be suspended for diagnosis. The patient may assume a standing, kneeling or reclining position during examination. The primary patient support couch is designed to accommodate the upper portion of the body in substantially the same way regardless of whether the patient is kneeling, standing or reclining. In the standing position, the patient merely leans over the top of the primary support couch. Accessories are provided in the form of a step platform, kneeling bench and foldable vanity screen. The present invention is directed to a combination vanity screen and patient support couch extension. These accessories permit the ultrasound scanning apparatus of the applicant's prior application to be used by a patient in a variety of positions.

SUMMARY OF THE INVENTION

The present invention relates to a combined vanity screen and patient support couch extension which comprises two panels hinged together in overlapping relationship. The lower panel is an upright support panel which is rigidly supported either in a free-standing manner or by connection to an associated step platform. A couch extension panel is hinged in overlapping relationship to the top of the vertical support panel. A lock is provided to lock the two panels together vertically in a coplanar orientation. The lock comprises a conventional striker, mounted on the overlapping portion of the extension panel, and a conventional lock bolt and door knob assembly, mounted on the vertical support panel in such a way as to allow the bolt to engage the striker plate and hold the extension panel in the upright position to act as a vanity screen.

The free upper end of the extension panel includes a support which rests against projections mounted on the cabinet for the primary patient support couch. A latch is provided on the free end of the patient support couch extension to lock the extension onto the projections when the couch extension is in the horizontal position, aligned in a coplanar relationship with the primary support couch to act as an extension for the primary support couch.

A counterbalancing system is provided to facilitate the easy movement of the extension panel between the horizontal position, where it acts as a patient support couch extension, and the vertical position, where it acts as a vanity screen. This counterbalancing system includes a series of springs having one end affixed to a bracket mounted on the vertical support panel. The other end of the springs are connected to a second bracket, which is in turn connected to a strap connected to the same end of the extension panel to which the striker plate is affixed. The strap may be a fabric strap having transverse ribs. The strap is wound on itself through belt buckles to provide a high friction clasp for holding the belt so that it will not slip.

The overlapping relationship of the vertical support panel and the extension panel permit the panels to be hinged together at one point spaced apart from the point where they are locked together in the vertical position. Thus, forces which are likely to be experienced by the extension panel when it is in the vertical, vanity screen orientation are easily counteracted by the lock mechanism, since it is spaced apart from the hinge. The spacing of the lock mechanism away from the hinge provides a moment arm to counteract the forces which could destabilize the vanity screen if the lock and the hinge were not spaced apart.

In the preferred embodiment, the support panel and the extension panel each include a base section and a body section. The base section of the vertical support panel is longer than the body section. Conversely, the base section of the extension panel is shorter than the body section. Thus, when the support panel and the extension panel are placed in overlapping relationship, they fit together in overlapping relationship in the fashion of an extended lap joint commonly used in the carpentry trades.

These and other features and advantages of the present invention will become apparent from the following detailed description of the preferred embodiment taken in conjunction with the following drawings:

BRIEF DESCRIPTION OF THE DRAWINGS

FIG. 3 shows a detailed view of the locking mechanism;

FIG. 4 shows a detailed cross-sectional view of the locking mechanism for locking the two panels in the vertical position;

FIG. 5 shows a detailed sectional view of the latching mechanism for latching the free end of the extension panel to the cabinet of the primary support couch;

FIG. 6 shows a further detailed view of the latching mechanism of FIG. 5;

FIG. 7 shows a detailed cross-sectional view of the hinge which connects the upright panel to the extension panel;

FIG. 8 shows a detailed view of the counterbalance assembly;

FIG. 9 shows a schematic view of the belt used in the counterbalance system;

FIG. 10 shows a detailed view of another portion of the counterbalance system; and, FIG. 11 shows an exploded perspective view of the latch mechanism shown in FIGS. 5 and 6.

DETAILED DESCRIPTION OF THE PREFERRED EMBODIMENT

Figure 1:
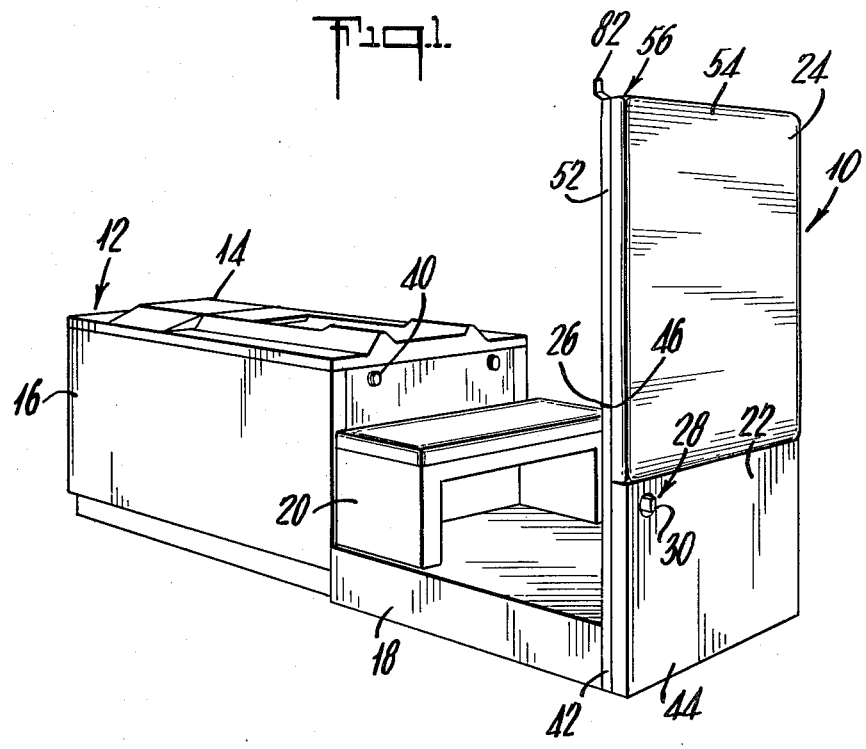
FIG. 1 shows a perspective view of the primary patient support couch and its associated cabinet together with accessories including a step up platform, a kneeling bench and the combination vanity screen patient support couch extension of the present invention, with the couch extension panel locked in the raised position to form a vanity screen.
Figure 2:
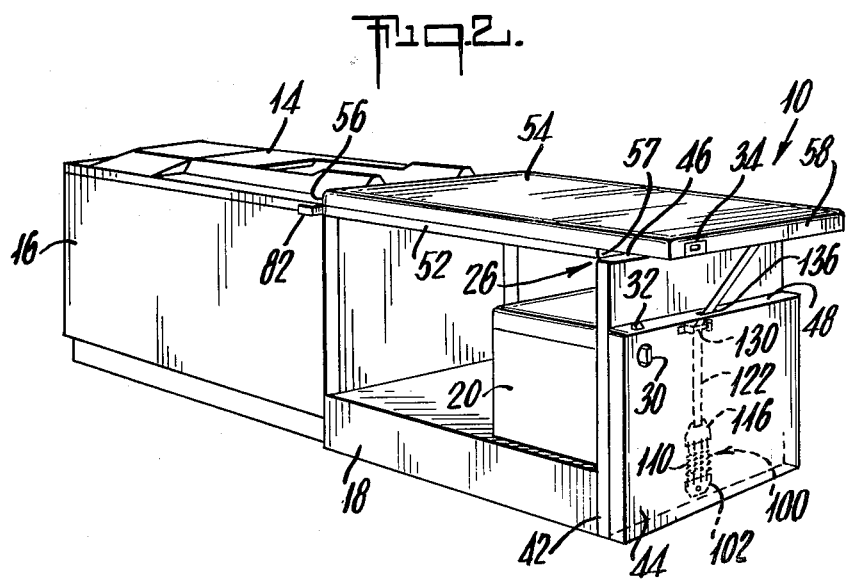
FIG. 2 shows a perspective view of the apparatus shown in FIG. 1 with the couch extension panel in the horizontal position to provide a couch extension.

FIGS. 1 and 2 show the combined vanity screen patient support couch extension 10 as it is used with a particular kind of medical diagnostic equipment, namely, an ultrasound mammary scanning system 12, including a primary patient support couch 14 supported on the top of cabinet 16. Also included is a step platform 18, to which the combination variety screen couch extension 10 may be connected, and kneeling bench 20. The step platform and the kneeling bench will not be discussed further in this application. The ultrasound mammary scanning system will only be discussed to the extent that its cabinet 16 serves to support the couch extension of the present invention as an extension for the primary support couch 14.

In FIG. 1, the combination vanity screen support couch 10 is shown in the vertical position, where it acts as a vanity screen. In FIG. 2, combination vanity screen support couch extension 10 is shown in the horizontal position, where it acts as an extension for the primary support couch 14.

Still referring to FIGS. 1 and 2, it can be seen that the combination vanity screen couch extension 10 includes a generally planar, vertically disposed support panel 22 and a generally planar extension panel 24, which is connected to vertical support panel 22 by a hinge 26 (shown particularly in FIG. 7). Hinge 26 permits the extension panel to be pivoted from the vertical orientation, where it acts as a vanity screen to the horizontal orientation, where it acts as a couch extension. The two panels 22 and 24 are connected together in overlapping relationship. Hinge 26 is placed at one overlap point, and a conventional style door lock 28, with a knob 30, bolt 32 and striker plate 34 (see FIG. 4), is mounted near the other overlap point. Lock 28 may be engaged to hold extension panel 24 in the vertical position or disengaged to permit extension panel 24 to pivot into the horizontal position perpendicular to vertical support panel 22.

When extension 24 is disposed in the horizontal position, it rests on projections 40 mounted on cabinet 16. A mechanism, shown more particularly in FIGS. 5, 6 and 11, is used to lock the couch extension 24 to projections 40 on cabinet 16.

As will be described in detail in conjunction with FIGS. 8, 9 and 10, extension panel 24 is counterbalanced to facilitate its movement between the vertical and horizontal positions.

During the remainder of this application, we will describe the construction and operation of the vertical support panel 22 and extension panel 24, principally in conjunction with FIGS. 1 and 2. We will then describe the hinge 26 and lock 28 and the way in which they cooperate with the overlapping relationship of panels 22 and 24 to provide stability to the extension panel 24 when it is in the vertical vanity screen position. This will be done in conjunction with FIGS. 3, 4 and 7. We will then discuss the mechanism for latching extension panel 24 to projections 40 in the horizontal position in conjunction with FIGS. 5, 6 and 11. Lastly, we will discuss the counterbalance system in conjunction with FIGS. 2, 8, 9 and 10.

Referring again to FIG. 1, it can be seen that panel 22 includes a base section 42 extending from the floor to hinge 26, and a body section 44 extending from the floor along base section 42 to a point short of the upper edge 46 of base section 42, where hinge 26 is attached. Vertical section 22 is fabricated from sheet metal, wood or some other suitable material, and body section 44 is bolted or welded or otherwise permanently affixed to base section 42. Referring now to FIG. 2, the extent which base section 42 extends beyond body section 44 is clearly shown. The upper end of body section 44 is closed to form end wall 48.

As shown best in FIG. 2, extension panel 24 is similarly constructed, with base section 52 extending from hinge 26 where it is connected to upper edge 46 of base section 42 of vertical panel 22. A body section 54 extends from the free upper edge 56 of base section 52 beyond the lower edge 57 of base section 52 a distance comparable to the distance end wall 48 of body section 44 is spaced from upper edge 46 of base section 42. Thus, when vertical panel 22 and extension panel 24 are placed vertically in coplanar relationship, body section 54 overlaps base section 42, and lower end wall 58 of body section 54 confronts upper end wall 48 of body section 44. Vertical support panel 22 and extension panel 24 overlap one another in the fashion of a lap-joint commonly referred to in the carpentry trades.

Referring now to FIG. 7, it can be seen that upper edge 46 of base section 42 is connected to lower edge 57 of base section 52 by means of hinge 26. Hinge 26 is affixed to the confronting surfaces 46 and 57 by means of bolts, rivets, screws or other suitable fastners. Hinge 26 may be one hinge which extends along the entire surfaces 46 and 57 or can be a plurality of separate hinges.

Referring now to FIGS. 2, 3 and 4, the mechanism for locking vertical support panel 22 and extension panel 24 in a vertical coplanar alignment, to act as a vanity screen, will now be described. Referring to FIG. 2, it can be seen that lock 28 includes a generally cylindrical knob 30 extending through body section 44 of vertical support panel 22. Bolt 32 projects through end wall 48 of body section 44 toward confronting surface 58 of body section 54. A striker plate 34 is disposed on surface 58 so as to receive bolt 32. The interaction of striker plate 34 and bolt 32 will maintain extension panel 24 locked in the vertical position with respect to vertical support panel 22. Referring now to FIG. 4, knob 30 operates a mechanism 60 for engaging bolt 32 in striker 34. In FIG. 4 it can be seen that lock mechanism 60 includes a spindle 62, one end of which is connected to knob 30, and the other end of which is connected to a bushing 64. Spindle 62 extends through housing 66 and includes an offset cam surface 68 to which bolt 32 is operatively connected by conventional means. As the user turns knob 30, bolt 32 will move in or out of engagement with striker 34, depending upon the direction in which knob 30 is turned. Lock housing 66 is bolted to base section 42 of vertical support panel 22.

It can be appreciated, particularly in connection with FIG. 1, that the overlapping, confronting relationship of the extension panel 24 and vertical support panel 22, when they are locked in the coplanar vertical alignment to form a vanity screen, provides a great stability for extension panel 24. The portion of body section 54 which overlaps base section 42 coacts with hinge 26 to prevent extension panel 24 from rotating in the clockwise direction, as shown in FIG. 1, away from the primary support couch. The lap joint construction of the two panels prohibits this rotation.

The interaction of the striker plate 34 and lock bolt 32 prohibits extension panel 24 from rotating in the counterclockwise direction in FIG. 1 toward primary couch 14 when the lock is engaged. The spacing of the striker plate and bolt interface away from hinge 26 provides a moment arm and a mechanical advantage which reduces the force transmission to the lock mechanism. Thus, forces which are likely to be experienced by extension panel 24, when it is in the vertical position, can be more readily counteracted by lock 28, because the lock mechanism is spaced apart from the hinge. This is the second feature of the overlapping lap-joint construction of the two panels which adds to the stability of the extension panel when it is in the vertical, vanity screen position.

Turning now to FIGS. 2, 5, 6 and 11, we will describe the mechanism for latching the free upper edge 56 of body section 54 of couch extension 24 to cabinet 16 of the primary patient support couch. As previously explained, projections 40 project from cabinet 16 of the primary support couch and form a support surface against which couch extension 24 may rest when it is lowered into the horizontal position to form an extension for the primary patient support couch. Projections 40 are shown best in FIG. 6 to be a generally cylindrical projection with a circumferential groove 41 spaced a short axial distance from the free end of projection 40. The other end of projection 40 is bolted, welded or otherwise permanently affixed to cabinet 16. It is possible to align the free upper edge 59 of body section 54 with the upper edge 56 of the base section 52 and just rest base section 52 on projections 40 or some similar support. However, we believe it preferable to provide a securement latch which will latch couch extension panel 24 in the horizontal position. Thus, in our preferred embodiment, edge 56 is slightly recessed from edge 59 of body section 54. As shown best in FIG. 11, bar 70 is permanently affixed by means of bolts 71 projecting through bores 73 to the upper edge 56 of base section 52 of extension panel 24. Bar 70 is spaced apart from the end 56 of base section 52. Spacers 74 provide the necessary space between edge 56 and bar 70, as shown in FIG. 5. As shown in FIG. 11, a pair of dovetail cutouts 72 are included on the lower edges of bar 70 to mate with the circumferential grooves 41 on projection 40. The cooperation of dovetails 72 and grooves 41 serve to restrain the sideways motion of couch extension 24 with respect to the primary patient support couch 14.

Still referring to FIG. 11, there is shown a latch bar 80 with a tab 82 projecting from one end. Latch bar 80 is placed between edge 56 of base section 52 and bar 70 in the space provided by spacers 74. Latch bar 80 includes some axially extending slots 84 in which spacers 74 ride, so that as the user pulls tab 82, latch bar 80 will slide back and forth transversely of extension panel 24. Latch bar 80 also includes two L-shaped slots 86. The downwardly projecting leg 88 of slots 86 fit over projections 40 when extension panel 24 is lowered into the horizontal position. By pulling tab 82, the user slides latch bar 80 so that the horizontal leg 90 of L-shaped slot 86 engages projection 40 to lock extension panel 24 in the horizontal position about projections 40.

The counterbalance mechanism will now be described in connection with FIGS. 2, 8, 9 and 10. As previously described in connection with FIG. 2, the combination vanity screen and couch extension 10 is equipped with a counterbalance system 100 which facilitates the easy movement of extension panel 24 between its vertical position to its horizontal position. As shown in FIG. 2, and more particularly in FIG. 10, counterbalance 100 includes a first bracket 102 bolted to base section 42 of vertical support panel 22 by means of bolt 104. Lower bracket includes four holes 106 into which one end 108 of coil springs 110 is inserted. The other end 112 of coil springs 110 is inserted into holes 114 in a similar bracket 116. Second bracket 116 is not connected to base 42. The end 118 of bracket 116 removed from holes 114 includes buckle 120 for receiving a strap 122. Strap 122 is preferably a fabric strap with transverse ribbing so that when the strap 122 is folded back on itself, its ribbing provides a high friction contact so that the strap will not slip. Alignment roller 130 is supported for rotation by means of two segments of angle iron 132 and 134, which are bolted to base section 42 just inside end wall 48 of body section 44 of vertical support panel 22. A slot 136 exists in end wall 48 of body section 44. Strap 122 is fed between the alignment roller 130 and the surface of base section 42. Alignment roller 130 acts as a guide for strap 122 through slot 136.

Referring now to FIG. 10, there is shown a bracket 138 affixed near the lower end of body section 54 of extension panel 24. One end of strap 122 is affixed to extension panel 24 near the lower end of body section 54 by means of bracket 138. The other end of strap 122 is fed through slot 136 between base section 42 and alignment roller 130, through buckle 120 on the upper end of bracket 116, through a second buckle 140, over alignment roller 130 and back again through buckle 140 so that the ribbed fabric of belt 122 will be folded back upon itself through buckle 140 to prevent belt 122 from slipping. The spring tension of springs 110 is adjusted by adjusting belt buckle 140. Thus, as the user unlocks lock 28 and tips extension panel 24 from its vertical position toward its horizontal position, strap 122 will pull against the force of springs 110 to allow extension panel 24 to lower into position slowly without banging.

The present invention has been described in conjunction with the preferred embodiment. Those skilled in the art will appreciate that many modifications and changes may be made in the preferred embodiment without departing from the present invention. It is, therefore, not intended to limit the present invention except as set forth in the attached claims.

We claim:

1. A combination vanity screen and patient support couch extension for use in combination with a primary patient support couch comprising:

a support panel having an upper transverse edge;
    an extension panel having:
        (i) a base section including a first transverse edge and a second transverse edge removed from said transverse edge and disposed in confronting relationship to said upper transverse edge of said support panel; and, (ii) having a body section attached to said base section and projecting beyond said second transverse edge and overlapping said support panel;

a hinge connecting said support panel upper transverse edge to said extension panel base section second transverse edge, said hinge permitting said extension panel to be rotated from a first position, in generally coplanar alignment with said support panel to act as a vanity screen, to an extension position generally transverse to said support panel in generally coplanar alignment with said primary patient support couch, to act as an extension therefor;

selectably engageable locking means cooperatively disposed on said support panel and said extension panel for locking said support and extension panels together in a generally coplanar alignment; and, support means cooperatively disposed on said primary patient support couch and the first transverse edge of said extension panel for supporting said second panel in generally coplanar alignment with the patient support surface of said primary patient support couch.

2. The apparatus of claim 1 wherein said support panel includes a base section and a body section attached to said base section and said base section projects beyond said body section so that when said support and extension panels are hinged together and positioned in generally coplanar alignment, the body section of the extension panel overlaps the base section of the support panel and abuts the body section of the support panel to form a "lap-joint" type interface between said support and extension panels with the confronting surfaces of the base sections of said support and extension panels spaced apart from the confronting surfaces of the body sections of said support and extension panels.

3. The apparatus of claim 1 wherein said locking means includes a striker plate disposed on the end of the body section of said extension panel and a bolt projecting from the end of the body section of said support panel into engagement with said striker plate so that the interaction of said bolt and said striker plate will prevent the extension panel from pivoting about said hinge with respect to said support panel;

the overlapping end of said body section of said extension panel projecting sufficiently beyond said hinge to space the locking means sufficiently away from said hinge so that the locking means may easily counteract tipping forces which said extension panel is likely to experience when said extension panel is in the vanity screen position; said locking means further including a rotating knob for selectably engaging or disengaging said bolt from said striker plate.

4. The apparatus of claim 3 wherein said bolt is recessed within said body section of said support panel, and said knob projects through said body section of said support panel for ready access by a user.

5. The apparatus of claim 1 wherein said support means includes a generally cylindrical projection extending from said primary patient support couch and having a generally circumferential groove; and, a bar affixed to the first transverse edge of the base of said extension panel and including a dovetail notch aligned with said groove so that said bar may fit into said groove to provide a support for said extension panel when it is positioned for generally coplanar alignment with the primary patient support couch.

6. The apparatus of claim 5 further including a latch slidably supported between the confronting surfaces of the first transverse edge of the base of said extension panel and said bar and including a generally "L" shaped slot;

whereby when said latch is slid transversely to said extension panel, said "L" shaped slot will engage said projection to prevent said extension panel from being moved out of coplanar alignment with said primary patient support couch.

7. The apparatus of claim 1 further including a counterbalance means for counterbalancing the weight of said extension panel as it is being moved between said first and said second positions.

8. The apparatus of claim 7 wherein said counterbalance means includes:

a first bracket fixed to said support panel;

spring means having one end affixed to said first bracket and having a second end;

a second bracket affixed to the second end of said spring means;

an alignment roller affixed to said support panel and spaced apart from said second bracket;

clamp means affixed to the overlapping end of the body section of said extension panel;

adjustable belt means affixed between said second bracket and said clamp means and engaging said alignment roller and adjusted to permit said spring means to counterbalance the weight of said extension panel as it is being moved between said first and second positions.

9. The apparatus of claim 8 wherein said belt is a fabric belt with transverse ribbing; and, further including a belt buckle through which said belt is threaded to permit said belt to be folded against itself and to permit said transverse webbing to create a high friction force to prevent said belt from slipping.

10. A combination vanity screen and patient support couch extension for use in combination with a primary patient support couch comprising:

first and second generally planar panels disposed in overlapping relationship, having first and second overlapping edges;

hinge means connected to an overlapping edge of one of said overlapping panels and connected to the confronting back of the other of said overlapping panels; and, locking means disposed on the front of the second panel and engaging the second overlapping edge of the first panel so that said locking means and said hinge means are spaced apart by the distance which said first and second panels overlap.

* * * * *